United States Patent
Griffiths et al.

(10) Patent No.: US 7,534,631 B2
(45) Date of Patent: May 19, 2009

(54) APPARATUS FOR MEASURING SEMICONDUCTOR PHYSICAL CHARACTERISTICS

(75) Inventors: Carl Griffiths, Lianfechain (GB); Andrew Stafford, Gyffin (GB)

(73) Assignee: Optical Reference Systems Limited, St. Asaph (GB)

( * ) Notice: Subject to any disclaimer, the term of this patent is extended or adjusted under 35 U.S.C. 154(b) by 0 days.

(21) Appl. No.: 11/463,759

(22) Filed: Aug. 10, 2006

(65) Prior Publication Data

US 2007/0054425 A1 Mar. 8, 2007

(30) Foreign Application Priority Data

Aug. 11, 2005 (GB) .................. 0516477.7

(51) Int. Cl.
 *G01R 31/26* (2006.01)
(52) U.S. Cl. ...................................................... 438/16
(58) Field of Classification Search ............. 356/237.1, 356/302–307, 239.7, 244, 246, 445, 504; 438/16

See application file for complete search history.

(56) References Cited

U.S. PATENT DOCUMENTS

| | | | | |
|---|---|---|---|---|
| 3,895,873 A | * | 7/1975 | Dennison et al. ............ | 356/312 |
| 3,986,778 A | * | 10/1976 | Mathisen et al. ............ | 356/244 |
| 3,999,860 A | * | 12/1976 | Demsky et al. ............. | 356/402 |
| 4,111,563 A | * | 9/1978 | Tamm ....................... | 356/244 |
| 4,443,072 A | * | 4/1984 | Ballard ..................... | 359/509 |
| 4,473,295 A | * | 9/1984 | Doyle ....................... | 356/244 |
| 4,606,935 A | * | 8/1986 | Blum ........................ | 438/770 |
| 4,708,478 A | * | 11/1987 | Andrews et al. ............ | 356/244 |
| 4,989,974 A | * | 2/1991 | Anton et al. ................ | 356/246 |
| 5,009,485 A | * | 4/1991 | Hall ......................... | 359/586 |

(Continued)

FOREIGN PATENT DOCUMENTS

EP 0431415 A2 6/1991

(Continued)

OTHER PUBLICATIONS

Irvine; S. J. C., et al. "In Situ Characterization Techniques for Monitoring and Control of VPE Growth of HG2-XCDXTE", Semiconductor Science and Technology, Jun. 1, 1993, pp. 860-871, vol. 8, No. 6S; Bristol, GB.

(Continued)

*Primary Examiner*—Patrick J Connolly
*Assistant Examiner*—Scott M Richey
(74) *Attorney, Agent, or Firm*—Reising Ethington P.C.

(57) ABSTRACT

A reflectometry method and apparatus for gathering reflectance data indicative of one or more characteristics of a semiconductor substance being grown on a substrate within a reaction chamber. The method includes directing light of known characteristics from a light source into the reaction chamber towards the surface of the semiconductor at an acute angle, preferably 46°, and collecting the light reflected from the surface at a detector located on the other side of the chamber. The received light is then converted into electrical signals which are subsequently subjected to computer processing. The reaction chamber can have a rectangular cross-sectional shape with apertures cut in the two vertices of the reaction chamber located above the substance to thereby allow the light to pass into the reaction chamber at the acute angle and out again after having been reflected from the surface of the semiconductor.

18 Claims, 8 Drawing Sheets

U.S. PATENT DOCUMENTS

| | | | | |
|---|---|---|---|---|
| 5,159,410 | A | * | 10/1992 | Pollak et al. ................. 356/417 |
| 5,307,155 | A | * | 4/1994 | Ando et al. ................. 356/430 |
| 5,330,610 | A | * | 7/1994 | Eres et al. ..................... 117/86 |
| 5,350,923 | A | * | 9/1994 | Bassignana et al. .... 250/453.11 |
| 5,386,141 | A | * | 1/1995 | Liang et al. ................. 257/676 |
| 5,395,769 | A | * | 3/1995 | Arienzo et al. ................. 438/8 |
| 5,472,505 | A | * | 12/1995 | Lee et al. ..................... 118/715 |
| 5,552,327 | A | * | 9/1996 | Bachmann et al. ............ 216/60 |
| 5,705,403 | A | * | 1/1998 | Baek et al. ..................... 438/16 |
| 5,726,751 | A | * | 3/1998 | Altendorf et al. ........... 356/246 |
| 5,773,316 | A | * | 6/1998 | Kurosaki et al. .............. 438/16 |
| 5,807,761 | A | * | 9/1998 | Coronel et al. ................ 438/14 |
| 5,856,206 | A | * | 1/1999 | Baek et al. ..................... 438/32 |
| 5,968,379 | A | * | 10/1999 | Zhao et al. ............. 219/121.52 |
| 6,048,742 | A | * | 4/2000 | Weyburne et al. .............. 438/7 |
| 6,319,736 | B1 | * | 11/2001 | Baklanov et al. .............. 438/16 |
| 6,383,301 | B1 | * | 5/2002 | Bell et al. ................... 118/716 |
| 6,410,347 | B1 | * | 6/2002 | Baek et al. ..................... 438/7 |
| 6,541,287 | B2 | * | 4/2003 | Ino et al. ..................... 438/16 |
| 6,726,767 | B1 | | 4/2004 | Marrs et al. |
| 7,092,083 | B2 | * | 8/2006 | Chadwick et al. ........... 356/244 |
| 7,159,599 | B2 | * | 1/2007 | Verhaverbeke et al. ...... 134/109 |
| 2006/0183055 | A1 | * | 8/2006 | O'Neill et al. .............. 430/316 |

FOREIGN PATENT DOCUMENTS

| | | |
|---|---|---|
| EP | 0666337 A1 | 8/1995 |
| EP | 0814505 A1 | 12/1997 |
| GB | 2291890 | 2/1996 |
| JP | 3104212 | 5/1991 |

OTHER PUBLICATIONS

Rebey; A., et al. "In Situ Reflectance Monitoring of the Growth and Etching of AlAs/GaAs Structures in MOVPE", Journal of Crystal Growth, Elsevier, Feb. 1, 2004, pp. 450-457, vol. 261, No. 4; Amsterdam.

United Kingdom Search Report for Application No. GB0516477.7; Oct. 12, 2005, pp. 1-4.

European Search Report for Application No. EP06254216; Jan. 5, 2007, pp. 1-9.

* cited by examiner

APPARATUS FOR MEASURING SEMICONDUCTOR PHYSICAL CHARACTERISTICS

TECHNICAL FIELD

This invention is concerned with the measurement of one or more of the physical characteristics, attributes and/or properties of semiconductor materials in real time as they are grown, such measurement commonly currently being conducted using a technique known as in-situ reflectometry.

More specifically, the invention is concerned with the improvement of in-situ reflectometry techniques as they are applied to the measurement of Ga—N and Ga—Al—N semiconductor materials which have recently been more widely adopted in the semiconductor industry. However, those skilled in the art will appreciate that this invention is not restricted to such semiconductor materials, and indeed the invention may have application beyond traditional and more modern semiconductor materials. Moreover, from the following, it will be appreciated that the invention may improve in-situ reflectometry for any material which may be grown using any of a number of deposition techniques, such as Chemical Vapour Deposition (CVD), Metal Organic Vapour Phase Epitaxy (MOVPE), Molecular Beam Epitaxy (MBE) and the like.

BACKGROUND OF THE INVENTION

A modern reflectometry technique is usefully described in an article entitled "In-Situ Characterization During MOVPE Growth of III-Nitrides using Reflectometry" by Christoph Kirchner and Matthias Seyboth, working in the Department of Optoelectronics in the University of Ulm.

In this article, the authors describe an in-situ reflectometry technique during low pressure Metal Organic Vapor Phase Epitaxy (MOVPE) growth of GaN using a commercial fiber reflectometer.

Nitride based materials comprise today's fastest developing III-V compound semiconductor (In—Al—G a—N) technology. Excellent optical and electrical properties, a wide and direct bandgap in combination with high thermal, mechanical, and chemical robustness make GaN and its alloys a well suited material system for optoelectronic devices in the UV to visible frequency range (e.g. light emitting diodes (LEDs), laser, photodetectors).

Successful epitaxial growth of such multilayered device structures requires precise control of the growth parameters (temperatures, flows, pressures) to achieve reproducible results. In particular, the heteroepitaxial GaN growth on highly mismatched substrates requires a two-step growth process consisting of i. nucleation at low temperature to provide a nucleation semiconductor layer and annealing this layer, and then ii. subsequent semiconductor growth to achieve high quality epitaxial GaN layers.

Deposition and subsequent annealing of the nucleation layer is a critical, highly sensitive process, and reproducibility is a pervasive problem due to the fact that small variations of substrate temperature and slightly different morphologies of the sapphires of which the substrates are commonly constituted strongly influence properties of the nucleation layer and subsequent GaN growth. In-situ characterization methods would therefore be very helpful in controlling the initial growth stages of GaN as this could result in a more uniform, less flawed and more consistent semi-conductor material.

It is worth mentioning that one real-time semiconductor property characterization method in current use is known as reflection high electron energy deflection (RHEED), and this method is widely used in molecular beam epitaxy (MBE) to control two-dimensional growth, growth rates and composition of ternary layers. However, CVD does not involve high vacuum conditions and therefore RHEED cannot be applied.

In gas phase epitaxy (GPE) processes, or other semiconductor layering, deposition and growth techniques which are conducted in aggressive environments, in-situ reflectometry can provide similar access to the growth process.

The most common methods of growing GaN and like semiconductors is a process known as Gas Phase Epitaxy (GPE) or MOVPE, and such process is most commonly carried out using a piece of apparatus known as a reactor. Such reactors are manufactured by companies like Aixtron, Veeco, and EMF Limited. A specific example of a reactor, and one which is currently popular in the industry is an Aixtron AIX 200 RF. Essentially, the reactor is a horizontally orientated cylindrical chamber through which gas vapour is allowed to flow and which is radio-frequency heated and comprises a water cooled quartz reaction chamber operated at low pressure. Typically, Trimethylgallium (TMGa), Trimethylindium (TMIn), Trimethylaluminum (TMAl) and ammonia are used as group III and group V precursors respectively and these are caused to pass over a substrate material, which is commonly sapphire ($Al_2O_3$).

Referring firstly to FIG. 1 provided herewith, the MOVPE system was equipped with a commercially available reflectometer schematically indicated at 2 consisting of a white light source 4 and a CCD spectrometer 6 (Filmetrics F 30). The spectrometer is a 512-element photodiode array with a spectral range of 400 nm-1100 nm and a resolution of 2 nm. The spectrometer is controlled by a computer 8 and the spectrometer software allows calculation of semiconductor physical characteristics such as deposition rate, the refractive index n, the extinction coefficient k and reflectivity. For these purposes, material data libraries are contained in the software.

As will be appreciated from FIG. 1, an optical access to the substrate with the nitride layer growing thereon in the MOVPE reactor is mandatory.

Accordingly, the reactor 10 comprises a liner tube 12 made of quartz glass. To the outside of the reactor, there is provided a water-cooled jacket 14, and to the outside of said jacket there is provided a radio-frequency heating coil 16 which acts to direct high intensity RF energy onto a susceptor 18 on top of which is positioned a substrate 20 which is most commonly made of sapphire. During use, a source of mixed metal organic gases passes into the chamber through an inlet 22 and as a result of the controlled conditions within the reactor and the composition of the inlet gas, semiconductor material begins firstly to nucleate on the substrate, and subsequently grow thereon. A source of purging gas is also provided which flows around the liner tube and whose flow ultimately aids in the expulsion of the metal organic gas stream from the reactor in general. It is to be understood that the nature of the gaseous flows used in such reactors is often exceptionally toxic to humans, and that great care must be taken in how such gases are handled.

In use, due to the horizontal configuration of the reactor, the ceiling of the liner gets coated with Nitride deposits during semiconductor growth, rendering it opaque to at least some extent. Therefore, a 5 mm diameter hole is drilled in the liner ceiling. The liner is located inside a quartz cylinder (outer reactor tube), which is surrounded by the water cooling jacket made of quartz, too. The reflectometer is mounted directly above the zenith of the usually cylindrical liner in which the hole is drilled so that, except for variations in the surface profile of the semiconductor, light incident thereon from the reflectometer is reflected directly back towards the source of the light as generally indicated at 26. Both the incident and reflected light has to pass through all the quartz walls and the cooling water. Disturbing reflections from the quartz walls can be eliminated by reference measurements as in generally the oscillatory characteristics of the quartz is not affected by reaction conditions.

The spectrometer and the light source are connected to the lens system 28 by optical fibers of a coaxial type, outer strands of which are intended to carry reflected light back to the spectrometer, and the inner strands of which are intended to carry white light from the white light source of the reflectometer. The reflectance of the sample surface, recorded during the growth process, is continuously monitored and recorded. After loading the substrate into the reactor, substrates are typically heated up to 950° C. under a steady flow of a nitrogen/hydrogen mixture. Following this sapphire surface cleaning step, the substrate temperature is lowered to 520° C. for the deposition of the low temperature nucleation layer. After the nucleation layer is deposited, reactor temperature is increased to 1050° C. for growth of undoped bulk GaN.

Reflectance profiles obtained with the above mentioned setup from MOVPE GaN growth processes on sapphire are shown in FIG. 2. The two curves were recorded during GaN growth on sapphire substrates with slightly different polishing delivered from different manufacturers. The deposition of the nucleation layer causes the first increase in reflectivity. During the following annealing step, while the polycrystalline nucleation layer is partially crystallizing, the reflection increases slightly and then drops. At this point the main GaN layer growth is started, revealing small oscillations with increasing amplitude due to decreasing surface roughness. In spite of the fact, that all growth parameters were kept constant, in the initial stages of GaN growth, the course of oscillations amplitudes in the two curves is totally different. While in the upper curve, the maximum amplitude is reached after two oscillations, the lower curve reaches maximum after four oscillations. This confirms, that heteroepitaxial GaN growth processes are very sensitive against every small variation of sapphire substrate properties. Development of the surface morphology is indicated by the course of amplitudes in the reflectance spectrum. After a few oscillation periods, the growth conditions are stabilized. The shown oscillations of the GaN growth correspond to a growth rate of 2 μm/hr. The thickness of the GaN which is grown during one oscillation can be approximately calculated using the following equation:

$$D_{GaN}[nm] = \lambda_m / 2n$$

where $\lambda_m$ is the measuring wavelength of the spectrometer in nm and n is the refractive index of GaN at the measuring wavelength. The oscillations are resonances of the layer system, where the resonator is formed by the GaN layer and the refractive index steps of the transitions GaN/sapphire and GaN/gas phase, respectively. In FIG. 2, one oscillation corresponds to a GaN layer thickness of around 118 nm, according to the above equation. The refractive index of GaN at the spectrometer wavelength of 580 nm is 2.45 and does not change much with temperature. Thus the values for thickness calculated during growth (hot substrate) agree well with data measured at room temperature using Scanning Electron Microscopy (SEM).

During ternary layer growth (InGaN, AlGaN), prereactions in the reactor between the different group III molecules and ammonia can occur, strongly affecting growth rates and composition. The intensity of the prereactions is dependent on pressure and temperature in the reactor during growth and the type and amount of group III molecules (e. g. TMGa, TEGa, TMAl). In-situ reflectometry provides direct information on any change of growth parameters (pressure, temperature, fluxes) affecting either growth rate (change of oscillation width) and/or surface roughness (change of oscillation amplitude).

Other technical articles, specifically one mentioning one of the inventors herefor, namely that published in the *Journal of Crystal Growth* 248 (2003) 533-536, clearly demonstrate the strong interaction between growth conditions, the substrate surface preparation, and the physical properties of GaN epilayers.

It is also to be noted that other characterisation methods for determining physical properties of semiconductors are available, such as transmission or scanning electron microscopy (T/SEM), high resolution X-ray diffraction (HR-XRD), photoluminescence (PL) and capacitance-voltage (C-V), but such are not suited or indeed impossible to conduct in real-time during the semi-conductor growth process due to the aggressive ambient conditions within the reactor.

There are a number of difficulties associated with the above described in-situ reflectometry technique. Firstly, the coaxial structure of the coaxial fiber optic cable used in the reflectometer, necessitates expensive focussing and light reception optics.

Secondly, the operating temperature of the reactor is commonly in excess of 1000° C., and to ensure that the water does not boil in the cooling jacket, it must be pumped therefore at a sufficient flow rate so that the heat of the reactor can be safely transmitted to the water and thus removed. The difficulty with this is arrangement is that the pumping of water through an essentially annular passageway at a substantial flow rate and pressure necessarily causes some degree of turbulence in the fluid. As a result, the effective refractive index of the fluid through which both the incident and reflected light must pass is slightly altered. It is also to be mentioned that the transfer of heat to the cooling water can also cause some slight change in the refractive index, and therefore any measurements taken from the reflectometer need to take account of this. A useful parallel the these phenomena is the twinkling of stars in a night sky, which is caused by exactly the same dynamic alteration in the refractive indices of space and the earth's atmosphere.

Indeed, the refractive indices of all the various fluids and solids through which the incident and reflected light pass needs to be taken into account in preparing useful data for analysis, and which might ultimately be used to determine the physical characteristics of the semiconductor under test.

It is an object of the following invention to provide an improved means for real-time monitoring of semiconductor characteristics during growth which overcomes the above problems, and provides improved data for analysis.

BRIEF SUMMARY OF THE DISCLOSURE

According to the invention there is provided a reflectometery technique for gathering meaningful reflectance data indicative of one or more characteristics of a substance being grown within a reaction chamber at the time of measurement, said technique including the steps of directing light from a light source of known characteristics into a reaction chamber towards the surface of the substance being grown therein, and collecting the light reflecting from said surface at a detector whereat the received light is converted into electrical signals which are subsequently subjected to computer processing, characterised in that the angle of incidence, and thus the angle of reflection of the light with the surface of the substance being grown is acute.

Preferably, the angle of incidence and reflection with the substance being grown is 46°.

Most preferably, the reaction chamber cross-sectional shape is polygonal, and apertures, preferably in the form of circular holes or cuts, are provided at suitable locations both axially of said reaction chamber and transversely of the cross-section such that the light from the source may pass into the reaction chamber to one side of the substrate on which substance growth occurs and emerge after being reflected from the surface of the substance being grown to a substantially opposite side of the cross-section of said reaction chamber. Most preferably, the substrate on which substance growth occurs is provided substantially centrally of the cross-section of said reaction chamber.

Most preferably, the reaction chamber is polygonal with at least two of the vertices of said polygon being disposed on either side of the substance being grown therein.

Most preferably, cuts or holes are provided in a first and second vertex of said polygon, said first and second vertices being a suitable distance axially of said reaction chamber to allow light from the light source to pass unimpeded through the first vertex to then impinge on the surface of the substance being grown, and subsequently be reflected therefrom through the cut or hole in the second vertex and subsequently towards the detector disposed to the alternate side of the reaction chamber from the light source.

Most preferably, the technique includes the further step of providing an outer jacket to the reaction chamber, and furthermore water cooling said outer jacket. Preferably the outer jacket is of a quartz material through which light may pass. It is to be mentioned that the outer jacket of the reaction chamber is generally continuous and forms part of a sealed system which is continuously purged. As mentioned above, the gases used in semiconductor growing techniques are noxious and highly toxic, and therefore despite the provision of apertures in the reaction chamber in accordance with the invention, none of the gases can actually escape from the system as a whole.

Most preferably the technique includes the steps of filtering the light incident on the detector according to its polarisation, in particular by applying a polarising filter to the detector to eliminate any unwanted polarity components of the light incident thereon.

It is worth mentioning that the polarity of the incident light is very important as far as obtaining meaningful reflectance data is concerned because certain components of the light are absorbed more than others on incidence with the surface of the substance being grown. Off-angle reflectance causes phase shifts (the basis of reflectometry) in the wavelength, and as such it is important to isolate only a single component of the light—the mathematical analysis of the data gained from this is complex and not relevant here, except to say that additional processing must be completed for off-angle reflectance data received.

According to a second aspect of the invention there is provided reflectometry apparatus for gathering meaningful reflectance data indicative of one or more characteristics of a substance being grown within a reaction chamber in real time during growth, said apparatus including a light source disposed to the outside of said reaction chamber which includes a substantially horizontal substrate on which the substance growth occurs, and a detector also disposed to the outside of the reaction chamber but on the opposite side of the reaction chamber to that at which the light source is disposed, said detector being capable of converting light into electrical signals which are subsequently subjected to computer processing, characterised in that the light source is disposed to one side of the reaction chamber so as to direct light thereinto such that it impinges on the surface of the substrate, or the surface of the substance being grown thereon, at an acute angle and is reflected away therefrom at a similarly acute angle to the detector, which is disposed to the alternate side of the reaction chamber from that of the light source when said reaction chamber is viewed in end elevation.

Most preferably, the reaction chamber cross-sectional shape is polygonal, with at least two of the vertices of said polygon being disposed on either side of the substance being grown therein, each of said two vertices having apertures provided therein at a suitable distance axially of said reaction chamber to allow light from the light source to pass unimpeded therethrough, said light subsequently reflecting off the surface of the substance being grown and thence through the second cut in the second vertex and subsequently towards the detector.

Preferably the reactor chamber is rectangular or square in cross-section, and the substrate on which substance growth occurs is disposed substantially centrally of the cross-sectional area.

Most preferably, the reaction chamber forms part of a known piece of reflectometry apparatus, such as the Aixtron Aix 200. Specifically, it is preferred that a substantially cylindrical water cooled out jacket is provided surrounding the reaction chamber, preferably of a quartz material, and that the light source and the detector are mounted proximate or adjacent the outside surface of the water cooled jacket.

Further preferably the reaction chamber is provided with a susceptor material which is excited to a desired temperature by one or more radio-frequency coils disposed around the outer or inner surface of the water-cooled outer jacket.

The reaction chamber is one in which semiconductor material is most expediently grown on the substrate, which is preferably of a sapphire material.

In a yet further aspect of the invention there is provided a reaction chamber in which there is disposed a susceptor block atop of which is disposed a substrate suitable for the growing of semiconductor materials, said chamber being elongate and substantially tubular such that gaseous semiconductor precursor material might be caused to flow therethrough, characterised in that a pair of apertures is provided to one side of a first imaginary line drawn through the geometric centre of the cross-sectional shape, a first of said apertures being disposed to one side of a second imaginary line perpendicular to the first, and the second of said apertures being provided to the other side of said second imaginary line.

Preferably the cross section of the reaction chamber is polygonal having a first vertex and a second vertex disposed on opposite sides of the second imaginary line, said apertures being coincident with said vertices.

Most preferably the cross-section of the reaction chamber is rectangular or square, and the apertures, in the form of cuts are provided in the vertices on either side of one of the faces of said chamber, said cuts or holes being deep enough to create apertures through the walls of said chamber.

The applicant herefor has found that despite the need for significantly more complex processing algorithms in the PC attached to the detector which processes signals received therefrom on account of the off-angle reflectance data being received, the resulting measurement, calculation and determination of physical characteristics is markedly improved when conducting reflectometry in the manner described.

A further advantage is that the quantity of gas escaping through the cuts or holes in the vertices of the rectangular chamber is practically nil, and this further improves the technique because it results in lower quantities of deposits on the inside surface of the outer, water cooled jacket, which in turn further diminishes the amount of light ultimately received at the detector and thus compromises the quality of measurement.

An additional advantage, and one which concerns semiconductor material manufacturers, is that the drilling of holes or making of cuts in the reactor compromises the quality of the material being grown therein, particularly when the hole is provided directly above the substrate. In the present invention, the applicants have not encountered any reduction or compromise in the material quality, and they perceive this as significant, particularly as there is belief that an aperture or hole drilled in the reactor immediately above the growing substrate does indeed have a prejudicial impact on the quality of the resulting semiconductor.

Although not described in great detail in this specification, the software loaded on the PC which is used to analyse the data received from the detector conducts a number of different processes. Firstly, the software includes algorithms which reduce beam twinkle. Secondly, a smoothing function is applied to the data received, and thirdly, and perhaps most importantly, the software includes algorithms which perform matrix transformations on the data to account for the fact that the data is received from light incident on and reflected from the semiconductor material in so-called "off-angle" manner, i.e. at an acute angle. The reader should be aware of a publication by John Lekner in this regard, entitled "Theory of reflection of electromagnetic and particle waves", Nijhoff/Kluwer (1987), ISBN 90-247 3418-5.

By using the apparatus and method described above, it is possible to grow semiconductor materials in a much improved and more expedient manner, in particular by drastically reducing spin-up time, improving semiconductor recipes, and avoiding semiconductor growth wastage.

Importantly, the provision of apertures in the corners of the reaction chamber does not appear to materially affect the growth characteristics of the semiconductor, which is not believed to be the case for normal reflectometery where a 5 mm aperture is cut in the reaction chamber immediately above the substrate and growing semiconductor.

A specific embodiment of the invention will now be provided by way of example with reference to the following drawings wherein:

BRIEF DESCRIPTION OF THE DRAWINGS

FIG. 3A shows an enlarged perspective view of the reaction chamber of the apparatus of FIG. 3.

DETAILED DESCRIPTION

Figure 1:
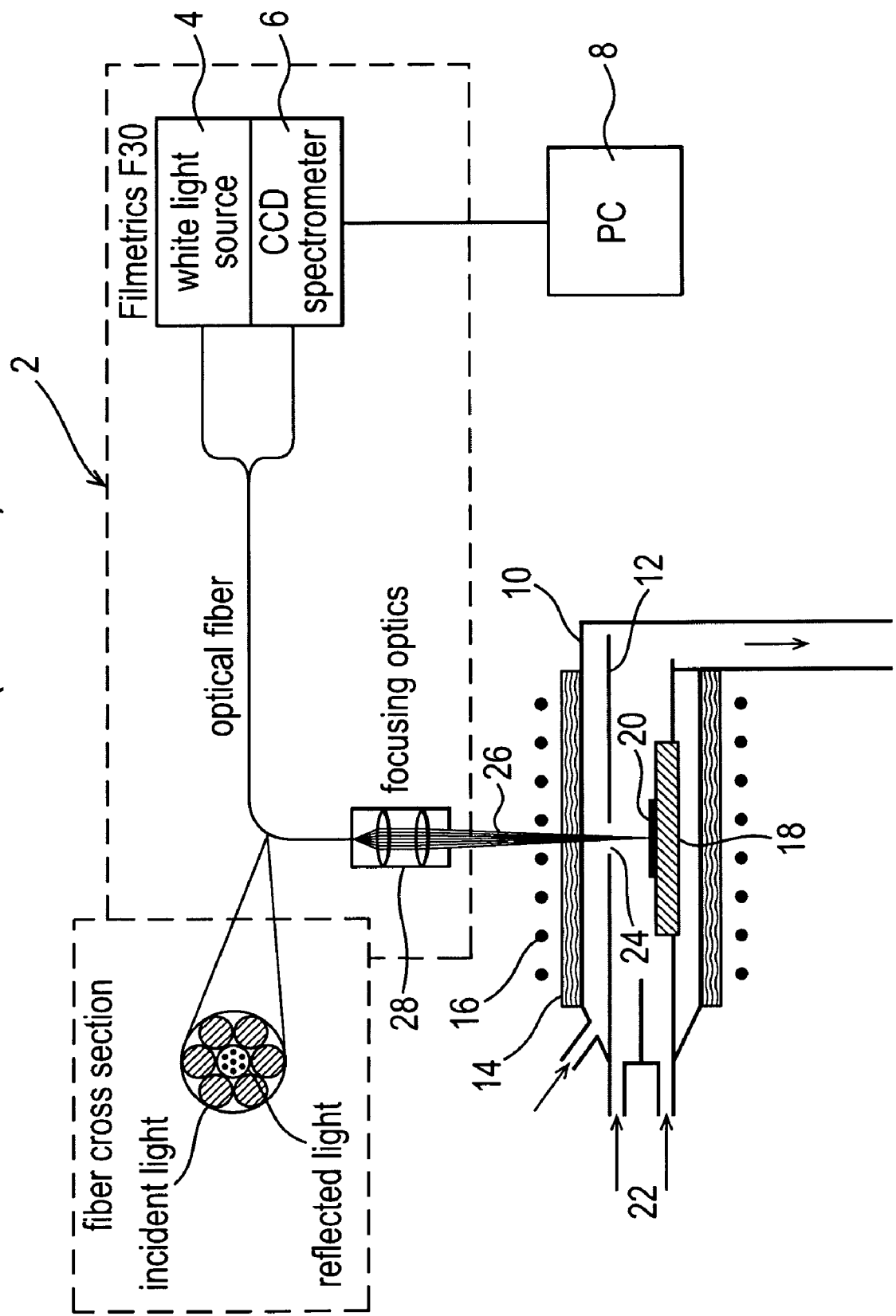
FIG. 1 shows a schematic representation of the prior art, in particular of an Aixtron AIX 200 RF horizontal MOVPE reactor.
Figure 2:
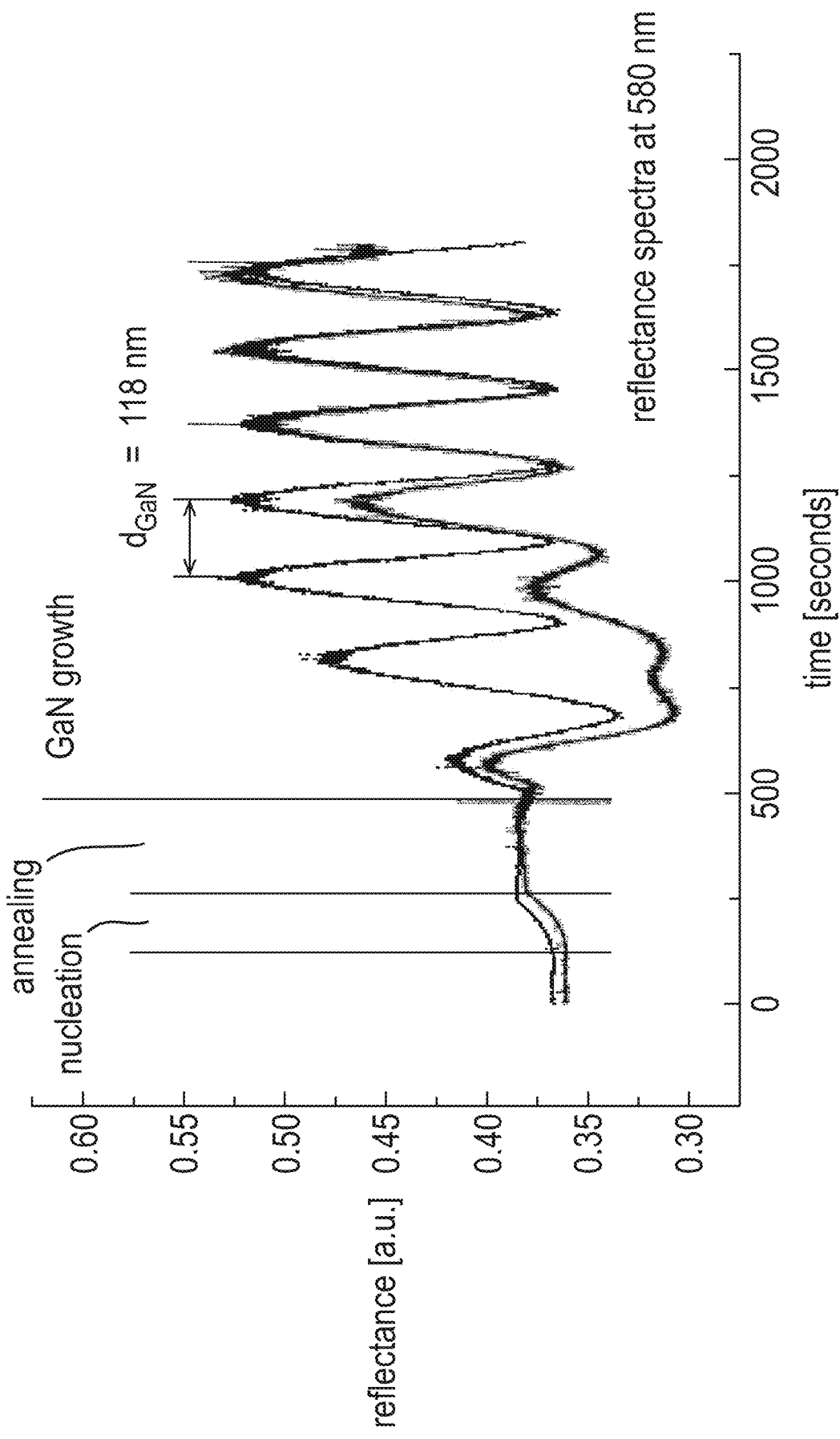
FIG. 2 shows a graph of in-situ reflectance spectra obtained during MOVPE growth of GaN-the two curves represent different sapphire substrates and therefore indicate strong differences in the initial stages of growth.
Figure 3:
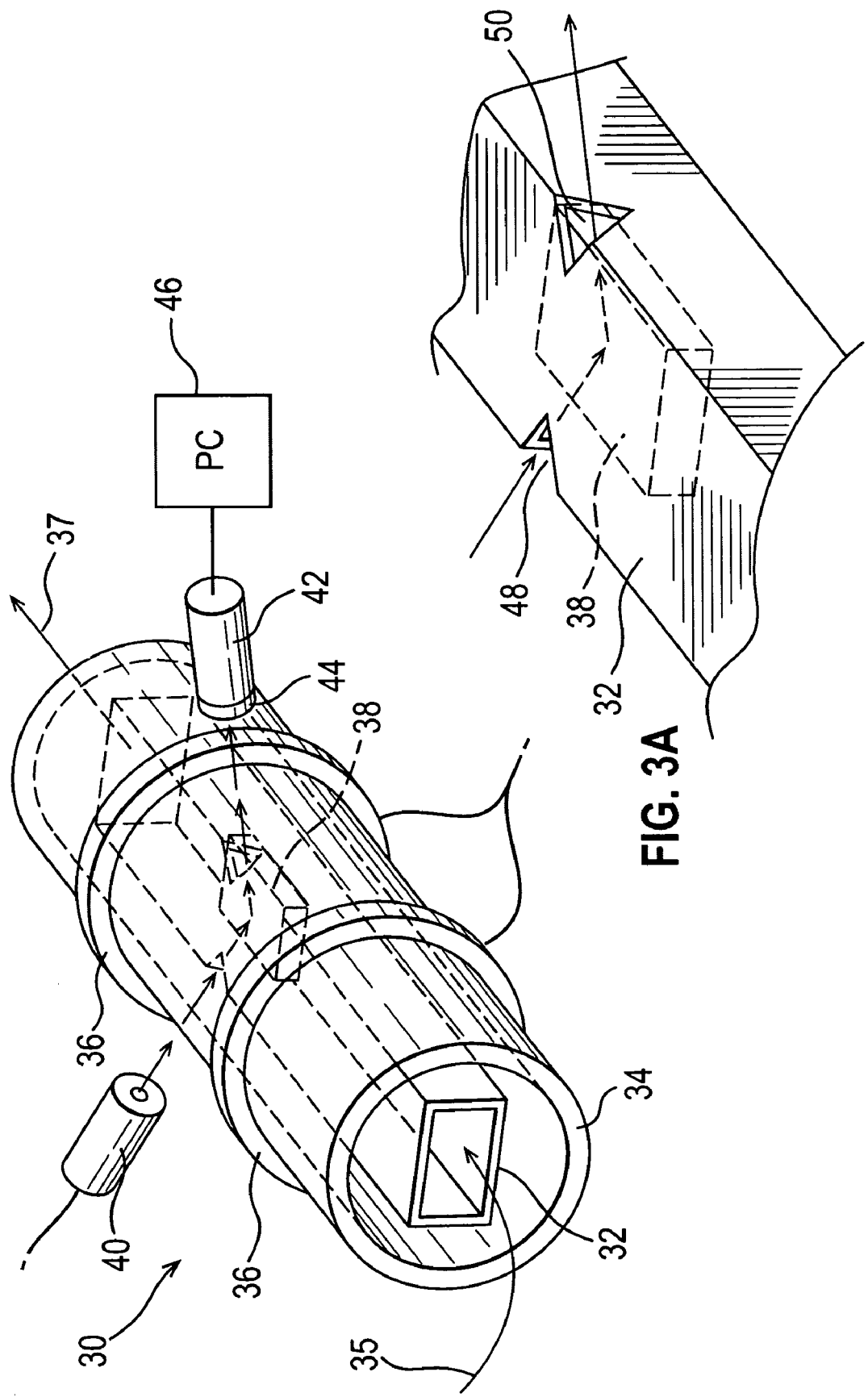
FIG. 3 shows a schematic perspective view of the apparatus according to the invention.

Referring to FIG. 3, there is shown a schematic view of a semiconductor growing apparatus 30 according to the invention having a reaction chamber 32 of rectangular cross-section, and outer jacket 34 which is water cooled, possibly by means of this outer jacket being constituted of two concentric glass cylinders having a gap therebetween through which water can be pumped.

To the outside of the outer jacket there is provided one or more radio-frequency heating coils 36 which provide a source of intense RF energy to the susceptor block indicated generally at 38 and disposed on the inside of the reaction chamber 32. A substrate, typically of sapphire, is positioned on said block 38, and it is on this substrate which semiconductor growth occurs.

In use, a source of semiconductor pre-cursor material is cause to flow (under entirely hermetic conditions, given its toxicity) through the inside of the reaction chamber, as shown at 35, over the substrate and expelled under controlled conditions as indicated at 37. This gas, and subsequent metal organic gases which may be used during the growth process, may be heated strongly to over 500° C., and in certain instances to over 1000° C. It has long been known that semiconductor growth is highly susceptible to changes in pressure and temperature, and it is important to achieve relatively stable pressure and temperature inside the reaction chamber if uniform and useful growth is to be achieved.

In accordance with the invention, there is provided a source of light 40, which is preferably a laser, and a detector 42 covered at the light receiving end thereof with a polaroid filter 44 which eliminates unwanted components of the reflected laser light. A computer 46 is connected to the detector to analyse and process the data received. In use, the metal organic gas flows over the heated substrate and after a first initial nucleation stage during which the semiconductor material is first nucleated on the substrate, additional molecules of semiconductor are grown on the first layer. The laser light is directed from one side of the reaction chamber and from the outside of the water cooled outer jacket into the reaction chamber through a first aperture 48 provided at a suitable location in one corner of the reaction chamber at a suitable location axially thereof, onto the growing semiconductor material, and then out through a second aperture 50 provided in the opposite corner and in the same region axially of the reaction chamber.

Figure 4:
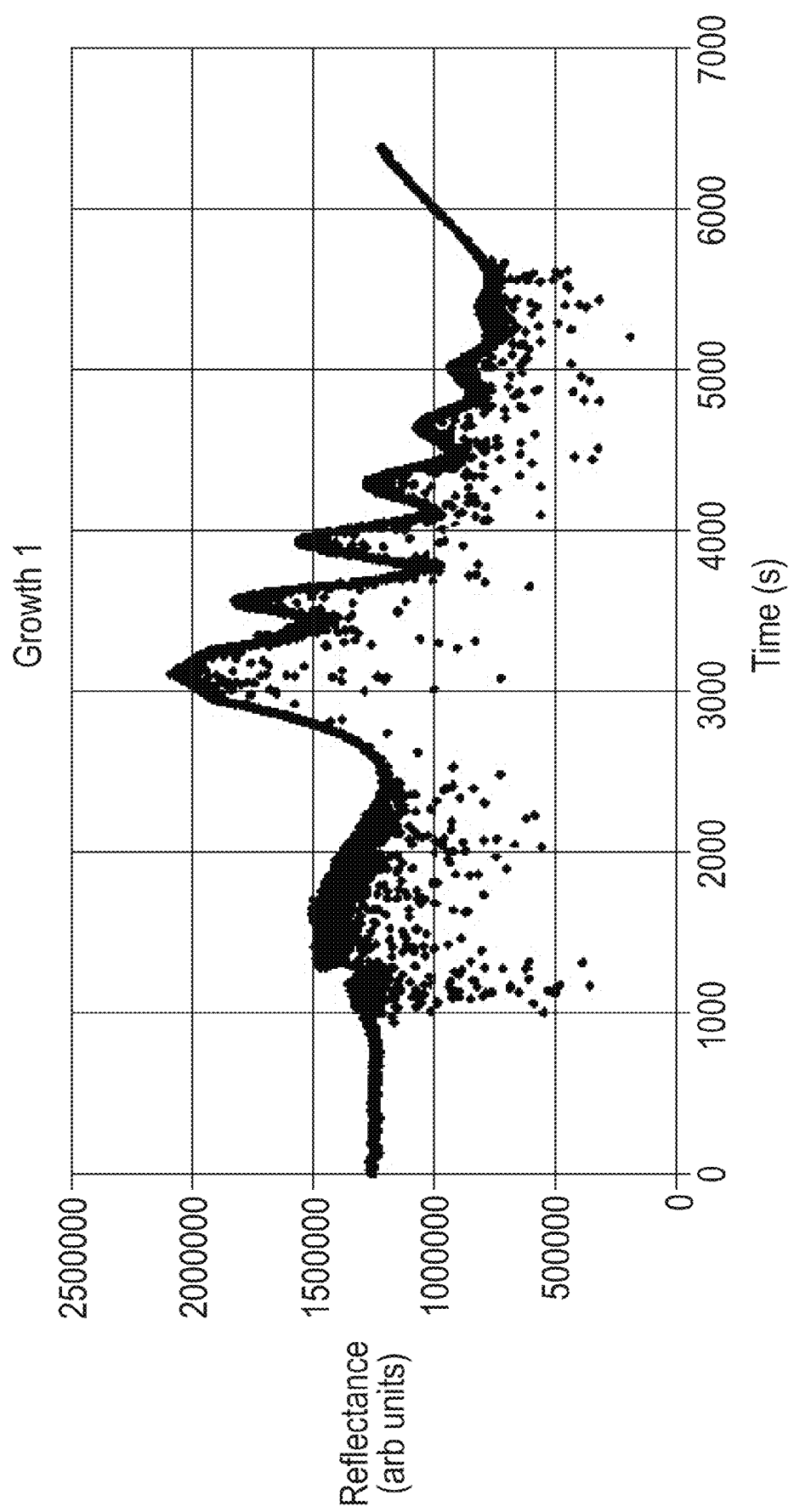
FIG. 4 shows a graph of data points obtained during a particular semiconductor growth run.
Figure 5:
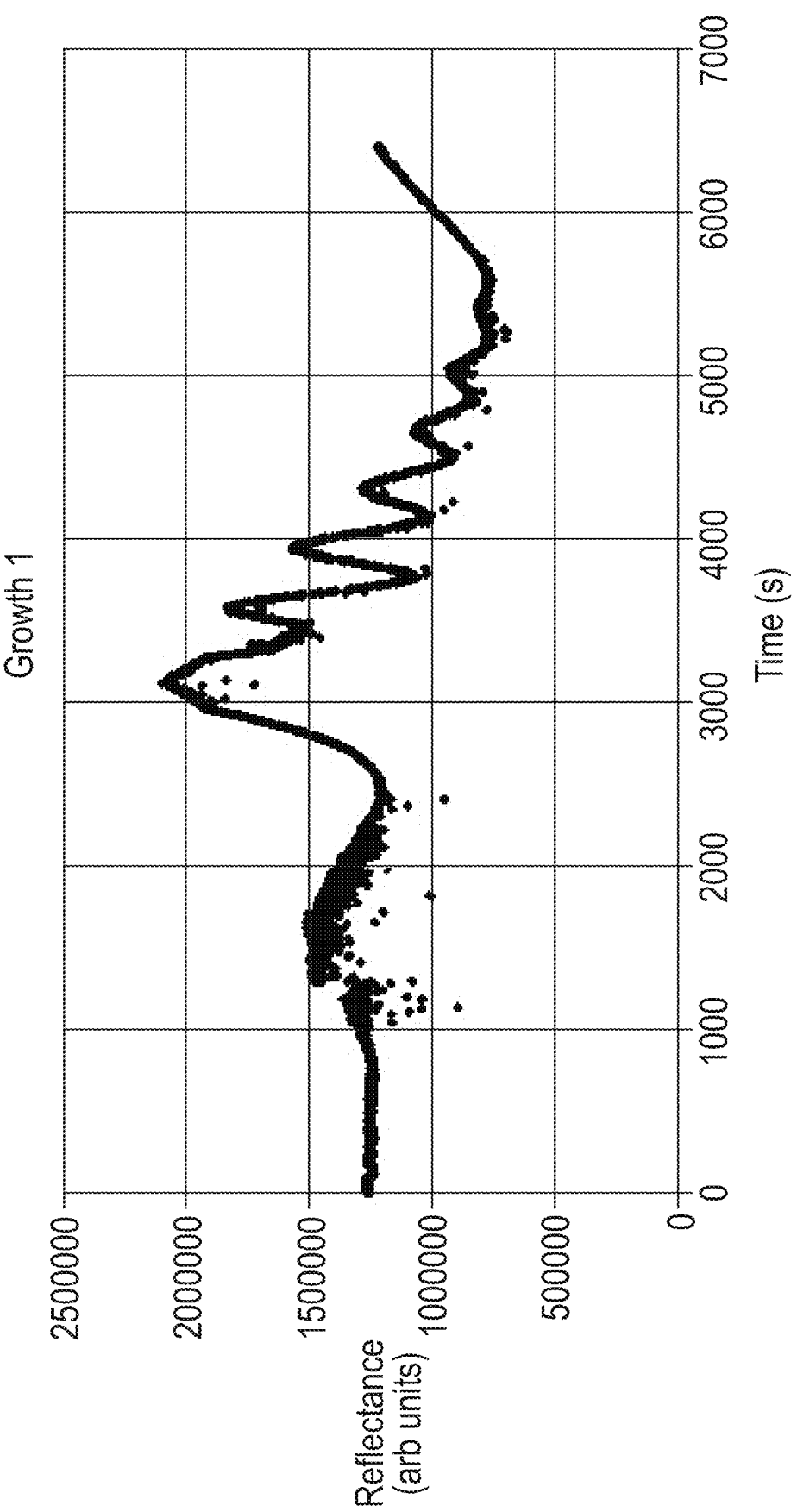
FIG. 5 shows the graph of data points of FIG. 4 after having been subjected to a simple filtering routing.

A typical growth run involves heating the susceptor to 1150° C. This creates a very significant amount of turbulence in the cooling water. In turn, this turbulence can cause the laser beam reflected from the substrate to move randomly by an estimated 1-2 mm. The physics behind this phenomenon is exactly the same as that behind the twinkling of distant street lights or of stars—the changes in density of the fluid through which the light passes results in subtle change in the refractive index of the fluid and hence in the optical path of the light. The consequence of twinkling in our application is that the laser beam can be deflected away from the second aperture in the reaction chamber, resulting in reduced intensity spikes in the data. This is clearly demonstrated in FIG. 4 which is a sample of raw data as collected during a particular growth run. After a simple filtering and spike removal routine is conducted on this data, a clearer set of data is obtained, as can be seen in FIG. 5.

Figure 6:
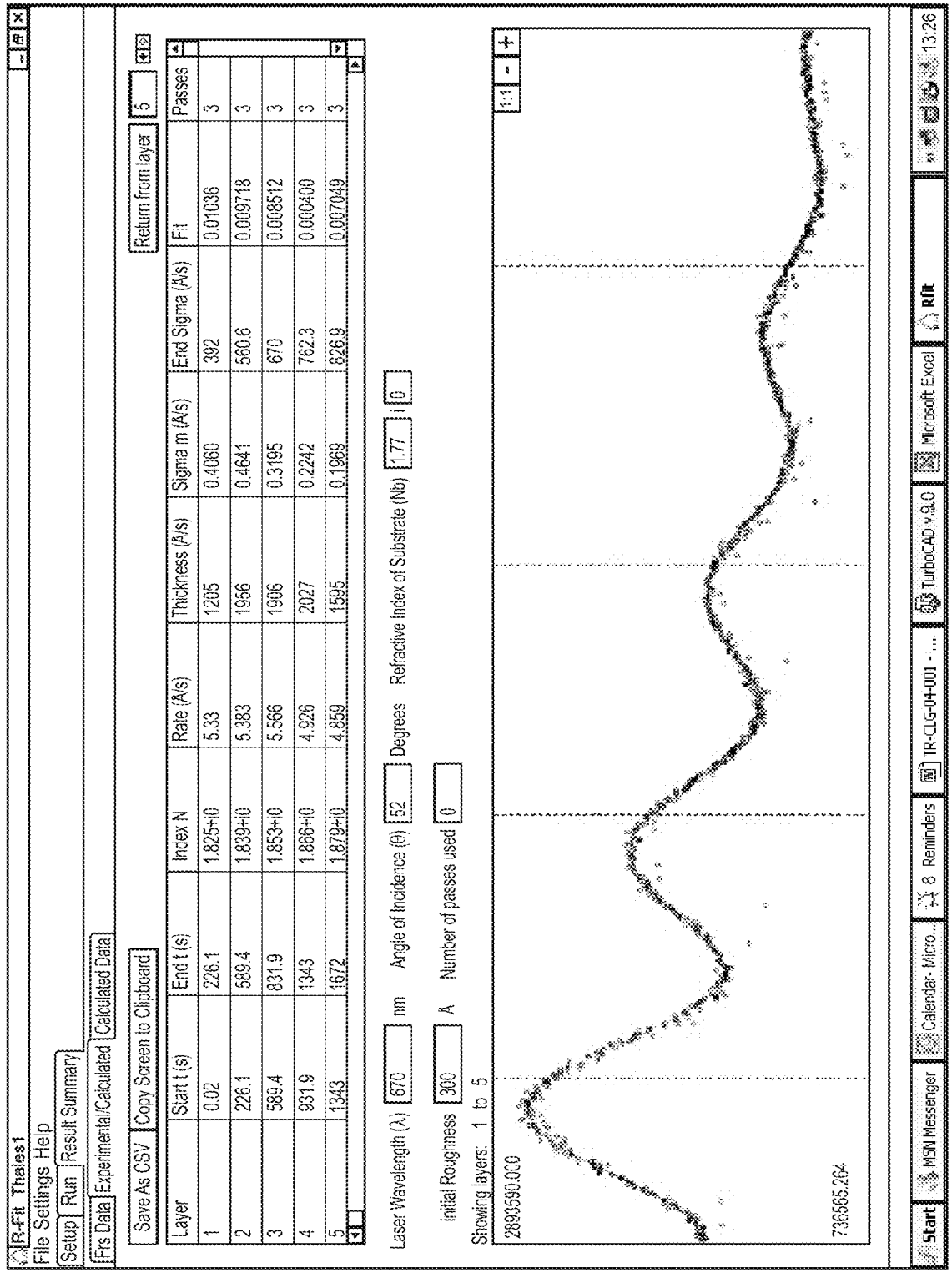
FIG. 6 shows the data of FIG. 5 after having been subjected to processing analysis.

This data can then be analysed using the proprietary R-Fit v2.1 Software program, which results in the data presented in FIG. 6.

Apart from the noise spikes which are largely removed, the data also has a substantial amount of high frequency, low-level random noise. This could be due to either;
a) A small but noticeable fluctuation in the transmission characteristics of the cooling water due to thermal effects or
b) The laser beam diameter being very close to the width of the exit slit in the inner liner. When this occurs, any slight movement in the reflected beam due to substrate wobble, twinkling or particles in the cooling water can cause it to graze against the exit slit and so reduce the light intensity arriving at the detector, i.e. marginal diffraction.

If the low-level noise is due to (a), then the most effective solution is to mathematically smooth the data. If the low-level noise is due to (b), then the best way to remove it is to reduce the diameter of the laser beam and/or increase the width of the exit slit. During this experiment the laser beam diameter was approximately 1.5 mm; it is possible to reduce it to less than 0.5 mm.

The main features to observe from the interferogram of FIG. 6 are;
a) the refractive index of GaN is too small and
b) the intensity of the oscillations falls off with time.

Figure 7:
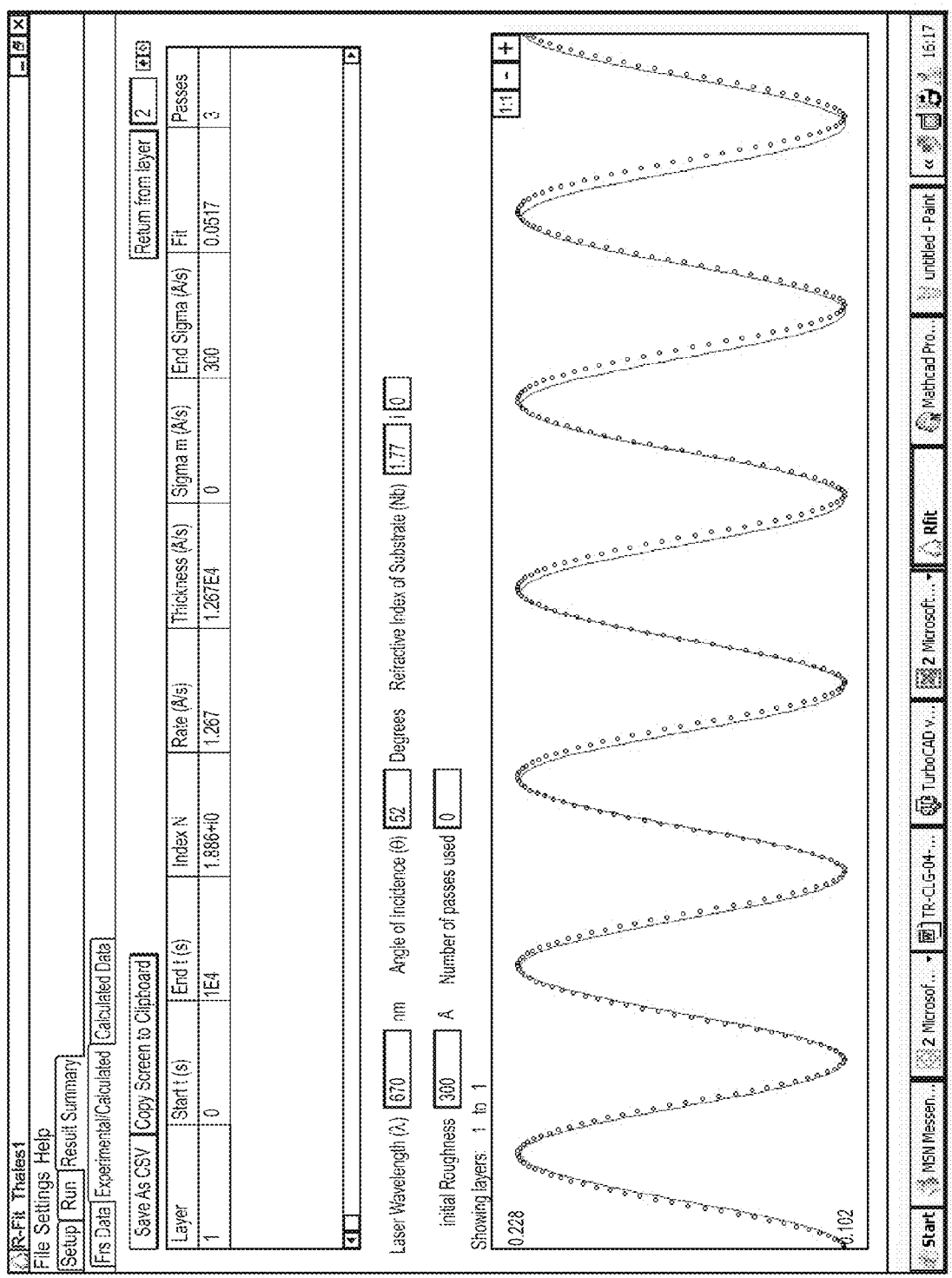
FIG. 7 shows a theoretical interferogram generated from GaN on sapphire with a light composed of 50% p- and 50% s-polarised light.

The refractive index of GaN should be around 2.19 whereas in order to achieve a fit, a value around 1.83 had to be used in the software. The reason for this discrepancy is that the reflectance system used under experimental conditions does not take into account the mixed polarisation of the laser beam. The mathematical model behind the R-Fit v2.1 software is based on p-polarised light only and the laser source used provided a mixed s- and p-polarised beam. This situation can be simulated by generating a theoretical interferogram from a layer of GaN on sapphire when it is illuminated with light composed of 50% s- and 50% p- polarisation, as shown in FIG. 7. In this case, the refractive index of GaN necessary to achieve a good fit is 1.86, less than the true value of 2.19 and close to the value of 1.83 used in the real data presented in FIG. 6.

It is for this reason that the polaroid filter 44 is employed to allow only p- polarised light through to the detector.

The reduction in the intensity of the oscillations is typical of a layer that is roughening and indeed a roughening factor is necessary in order to achieve the fit shown in FIG. 7. This was confirmed when the sample was removed from the reactor and subsequently analysed. It transpires that the roughnesses was a consequence of performing the growth with a recently cleaned liner and not as a result of introducing the two cuts in the inner liner since subsequent growths resulted in significantly smoother layers; see FIG. 8.

In a second growth run conducted using the experimental apparatus, a layer of GaN was deposited followed by a thinner layer of AlGaN. The interferogram recorded from this run is displayed in FIG. 8. This also demonstrated the effects of twinkling which resulted in data spikes which were removed using the same mathematical filtering routine as above. Likewise, the data has a certain degree of low-level high frequency random noise; most likely due to the closeness between the diameter of the laser beam and width of the exit slit. If this is the case then it can be removed by adjusting the laser beam diameter.

Figure 8:
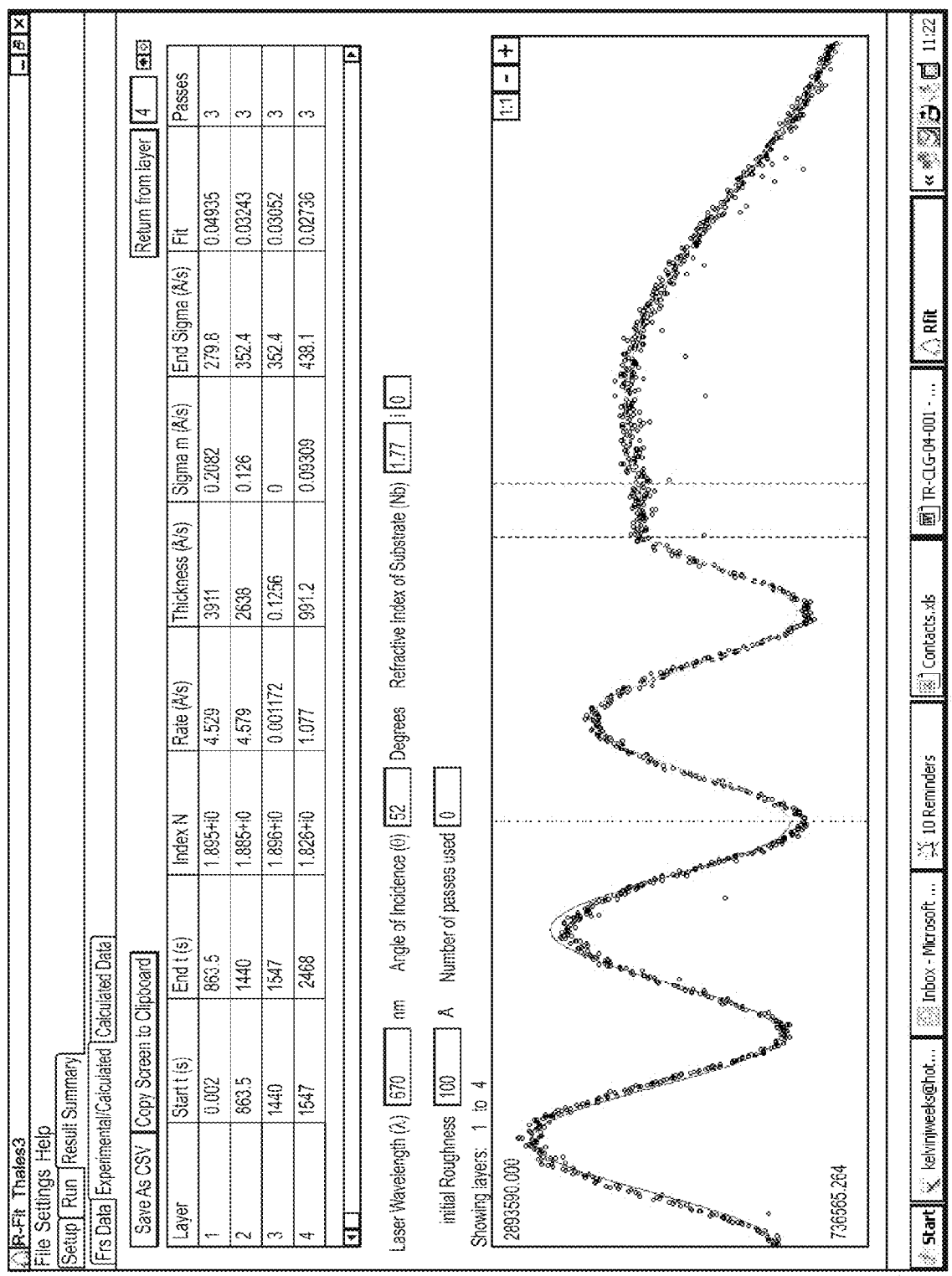
FIG. 8 shows a second interferogram generated from data collected during AlGaN on GaN growth on sapphire, after filtering and processing analysis, and after having data spikes removed.

The main features to note from the interferogram of FIG. 8 are:
a) the oscillations reduce in intensity only slightly and
b) after the third maxima, the rate of change of intensity is greatly reduced.

The smaller change in peak intensities is characteristic of a layer that is roughening slightly as it evolves. Again, a roughening factor had to be employed to achieve a good fit, but in this case the final rms roughness was less than half that necessary in the first growth run. Again, this was confirmed with post growth analysis; the layer looked to be as smooth as previous 'good' layers.

The change from GaN to AlGaN is very clear. At the boundary, there is a period of 107 s between the termination of the GaN layer and the beginning of the AlGaN layer. From the analysis presented in FIG. 8, it looks likely that during this time interval there was no significant loss of GaN due to sublimation—the substrate is still at 1150° C. at this stage and it is possible to inadvertently remove GaN during such pauses in growth.

The refractive index necessary to fit the AlGaN layer is less than that necessary for the GaN, entirely consistent with the known refractive index of this alloy, although because of the uncontrolled polarisation of the detected beam, the absolute value is inaccurate.

The rate of evolution of the AlGaN layer is significantly lower than was observed in the GaN case. From the analysis it looks to be between 15% 20% of the rate measured for GaN. Again, the polarisation effect prevents us from quantifying with any degree of accuracy the rate of film evolution and the film thickness, but it is possible to estimate that the AlGaN layer is approximately ⅛th the thickness of the GaN layer.

This it can be seen from this experimental data above that the procedure and apparatus according to the invention are of great advantage in determining various growth and physical characteristics of the semi-conductor being grown.

The invention claimed is:

1. A reflectometry method for gathering meaningful reflectance data indicative of one or more characteristics of a substance being grown within a reaction chamber at the time of measurement, the reaction chamber being elongate and substantially tubular such that gaseous semiconductor precursor material may be caused to flow therethrough along a direction substantially parallel to a longitudinal axis of the chamber, the chamber having a polygonal cross-section along a direction parallel to said longitudinal axis, the cross-section having first and second vertices disposed on either side of the substance being grown therein, said method including the steps of:
   directing light of known characteristics from a light source into the reaction chamber through an aperture in the first vertex of the polygonal cross-section and towards the surface of the substance being grown therein, and
   collecting the light reflecting from said surface and exiting the chamber through an aperture in the second vertex of the polygonal cross-section using a detector whereat the received light is converted into electrical signals which are subsequently subjected to computer processing, wherein the angle of incidence of the light with the surface is acute.

2. A method according to claim 1 characterized in that the angle of incidence and reflection with the substance being grown is 46°.

3. A method according to claim 1 characterized in that the apertures are provided at suitable locations both axially of said reaction chamber and transversely of the cross-section such that the light from the source may pass into the reaction chamber to one side of the substrate on which substance growth occurs and emerge after being reflected from the surface of the substance being grown to a substantially opposite side of the cross-section of said reaction chamber.

4. A method according to claim 3 characterized in that the substrate on which substance growth occurs is provided substantially centrally of the cross-section of said reaction chamber.

5. A method according to claim 3 characterized in that the apertures are in the form of circular holes.

6. A method according to claim 3 characterized in that the apertures are in the form of cuts.

7. A method according to claim 1 further comprising the step of providing an outer jacket to the reaction chamber.

8. A method according to claim 7 characterized in that said outer jacket is water cooled.

9. A method according to claim 7 characterized in that the outer jacket is of a quartz material through which light may pass.

10. A method according to claim 7 characterized in that the outer jacket of the reaction chamber is continuous and forms part of a sealed system which is continuously purged.

11. A method according to claim 1 characterized in that the method includes the step of filtering the light incident on the detector according to its polarization by applying a polarizing filter to the detector to eliminate any unwanted polarity components of the light incident thereon.

12. Reflectometry apparatus for gathering meaningful reflectance data indicative of one or more characteristics of a substance being grown, said apparatus including a reaction chamber which includes a substantially horizontal substrate on which the substance growth occurs, a light source disposed to the outside of said reaction chamber, and a detector also disposed to the outside of the reaction chamber but on the opposite side of the reaction chamber to that at which the light source is disposed, said detector being capable of converting light into electrical signals which are subsequently subjected to computer processing, characterized in that:

the reaction chamber having a susceptor block atop of which is disposed a substrate suitable for the growing of semiconductor materials, said chamber being elongate and substantially tubular such that gaseous semiconductor precursor material may be caused to flow therethrough along a direction substantially parallel to a longitudinal axis of the chamber from an inlet disposed at an end of the chamber, the chamber having a polygonal cross-section alone a direction parallel to said longitudinal axis, the cross-section having a first vertex and a second vertex with said first vertex having a first aperture and said second vertex having a second aperture;

the light source being disposed to one side of the reaction chamber with said apertures and vertices being located relative to each other and to said substrate such that light directed into said chamber through said first aperture from said light source impinges on the surface of the substrate, or the surface of the substance being grown thereon, at an acute angle and is reflected away therefrom at a similarly acute angle and exits the chamber through said second aperture after which it is collected by the detector, which is disposed to the alternate side of the reaction chamber from that of the light source when said reaction chamber is viewed in end elevation.

13. Apparatus according to claim 12 characterized in that the reactor chamber is rectangular or square in cross-section, and the substrate on which substance growth occurs is disposed substantially centrally of the cross-sectional area.

14. Apparatus according to claim 12 characterized in that a substantially cylindrical water cooled outer jacket is provided surrounding the reaction chamber.

15. Apparatus according to claim 14 characterized in that the water cooled jacket is made of a quartz material, and that the light source and the detector are mounted proximate or adjacent the outside surface of the water cooled jacket.

16. Apparatus according to claim 12 characterized in that the reaction chamber is provided with a susceptor material which is excited to a desired temperature by one or more radio-frequency coils disposed to the outside of said reaction chamber.

17. Apparatus according to claim 12 characterized in that the reaction chamber is provided with a substrate on which the semiconductor material may be grown, said substrate being of a sapphire material.

18. Reflectometry apparatus, comprising:

an elongate, substantially tubular chamber through which gaseous semiconductor precursor material can flow;

a susceptor block disposed in said chamber;

a substrate disposed on top of said susceptor block, said substrate being suitable for the growing of semiconductor materials;

wherein said chamber has a polygonal cross-sectional that includes a pair of vertices located at upper portions of said chamber above said substrate and being located on one side of a first imaginary line drawn through the geometric centre of the cross-sectional shape, a first of said vertices being disposed to one side of a second imaginary line perpendicular to the first imaginary line, and the second of said vertices being provided to the other side of said second imaginary line;

wherein said chamber includes a first aperture located at said first vertex and a second aperture located at said second vertex;

a light source disposed outside said chamber, said light source supplying light into said chamber through said first aperture; and a detector disposed outside said chamber, said detector being positioned to receive light from said light source that has reflected off the semiconductor material on said substrate and exited said chamber through said second aperture.

* * * * *